United States Patent
Pandey et al.

(10) Patent No.: US 10,423,077 B2
(45) Date of Patent: Sep. 24, 2019

(54) METROLOGY METHOD AND APPARATUS, COMPUTER PROGRAM AND LITHOGRAPHIC SYSTEM

(71) Applicant: ASML Netherlands B.V., Veldhoven (NL)

(72) Inventors: Nitesh Pandey, Eindhoven (NL); Zili Zhou, Eindhoven (NL); Armand Eugene Albert Koolen, Nuth (NL); Gerbrand Van Der Zouw, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/223,372

(22) Filed: Dec. 18, 2018

(65) Prior Publication Data

US 2019/0146356 A1    May 16, 2019

Related U.S. Application Data

(63) Continuation of application No. 15/279,860, filed on Sep. 29, 2016, now Pat. No. 10,191,391.

(30) Foreign Application Priority Data

Oct. 2, 2015   (EP) .................................. 15188190

(51) Int. Cl.
*G03B 27/42*   (2006.01)
*G01N 21/55*   (2014.01)
(Continued)

(52) U.S. Cl.
CPC ........ *G03F 7/70625* (2013.01); *G01B 11/272* (2013.01); *G01N 21/47* (2013.01);
(Continued)

(58) Field of Classification Search
CPC ............. G03F 7/70633; G03F 7/70625; G03F 7/70616; G03F 7/70641; G03F 7/7065;
(Continued)

(56) References Cited

U.S. PATENT DOCUMENTS 7,557,934 B2   7/2009   Hugers
7,969,577 B2   6/2011   Werkman et al.
(Continued)

FOREIGN PATENT DOCUMENTS

JP    2002-372406 A    12/2002
TW    2006-39593 A     11/2006
(Continued)

OTHER PUBLICATIONS

English-Language Abstract for Japanese Patent Publication No. 2002-372406 A, published Dec. 26, 2002; 2 pages.
(Continued)

*Primary Examiner* — Mesfin T Asfaw
(74) *Attorney, Agent, or Firm* — Sterne, Kessler, Goldstein & Fox P.L.L.C.

(57) ABSTRACT

Disclosed is a metrology apparatus for measuring a parameter of a lithographic process, and associated computer program and method. The metrology apparatus comprises an optical system for measuring a target on a substrate by illuminating the target with measurement radiation and detecting the measurement radiation scattered by the target; and an array of lenses. Each lens of the array is operable to focus the scattered measurement radiation onto a sensor, said array of lenses thereby forming an image on the sensor which comprises a plurality of sub-images, each sub-image being formed by a corresponding lens of the array of lenses. The resulting plenoptic image comprises image plane information from the sub-images, wavefront distortion informa- (Continued)

tion (from the relative positions of the sub-images) and pupil information from the relative intensities of the sub-images.

18 Claims, 7 Drawing Sheets

(51) Int. Cl.
*G03F 7/20* (2006.01)
*G01B 11/27* (2006.01)
*G01N 21/47* (2006.01)

(52) U.S. Cl.
CPC ............ *G03F 7/706* (2013.01); *G03F 7/7015* (2013.01); *G03F 7/70633* (2013.01)

(58) Field of Classification Search
CPC .. G03F 7/7085; G03F 9/7088; G03F 7/70141; G03F 9/7092; G03F 9/7049; G03F 9/7076; G03F 7/70158; G03F 9/7046; G03F 1/84; G03F 7/706; G03F 9/7026; G01N 21/956; G01N 2021/213; G01N 21/211; G01N 21/55; G01N 23/207; G01B 11/272; G01B 2210/56; G01B 11/26; G01B 11/24; G01B 11/30
See application file for complete search history.

(56) References Cited

U.S. PATENT DOCUMENTS

| 8,866,168 | B2 | 10/2014 | Bailey et al. |
| 9,977,340 | B2 | 5/2018 | Aben et al. |
| 2006/0003921 | A1 | 1/2006 | Schwarz et al. |
| 2006/0066855 | A1 | 3/2006 | Boef et al. |
| 2006/0219947 | A1 | 10/2006 | Van De Kerkhof et al. |
| 2008/0068609 | A1 | 3/2008 | Werkman et al. |
| 2011/0027704 | A1 | 2/2011 | Cramer et al. |
| 2011/0043791 | A1 | 2/2011 | Smilde et al. |
| 2012/0242970 | A1 | 9/2012 | Smilde et al. |
| 2013/0107259 | A1 | 5/2013 | Choi et al. |
| 2016/0274472 | A1 | 9/2016 | Mathijssen et al. |
| 2017/0097575 | A1 | 4/2017 | Pandey et al. |

FOREIGN PATENT DOCUMENTS

| TW | 2008-42280 A | 11/2008 |
| TW | 2012-07356 A | 2/2012 |
| WO | WO 2009/078708 A1 | 6/2009 |
| WO | WO 2009/106279 A1 | 9/2009 |
| WO | WO 2011/012624 A1 | 2/2011 |
| WO | WO 2013/143814 A1 | 10/2013 |
| WO | WO 2015/090839 A1 | 6/2016 |

OTHER PUBLICATIONS

International Search Report and Written Opinion of the International Search Authority directed to related International Patent Application No. PCT/EP2016/071505, dated Nov. 24, 2016; 13 pages.
Goodman, J.W., "Introduction to Fourier Optics," The McGraw-Hill Companies, Inc., 1996; pp. 101-106.
Non-Final Rejection dated Sep. 12, 2017 for U.S. Appl. No. 15/279,860, filed Sep. 29, 2016; 6 pages.
Non-Final Rejection dated Nov. 16, 2017 for U.S. Appl. No. 15/279,860, filed Sep. 29, 2016; 10 pages.
Final Rejection dated Jun. 12, 2018 for U.S. Appl. No. 15/279,860, filed Sep. 29, 2016; 11 pages.
Notice of Allowance dated Sep. 13, 2018 for U.S. Appl. No. 15/279,860, filed Sep. 29, 2016; 9 pages.
International Preliminary Report on Patentability of the International Search Authority directed to related International Patent Application No. PCT/EP2016/071505, dated Apr. 3, 2018; 8 pages.

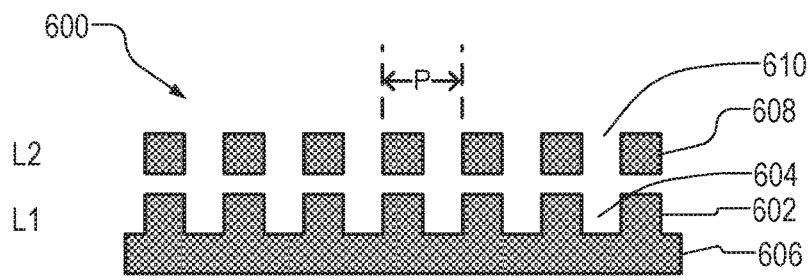
Fig 7A
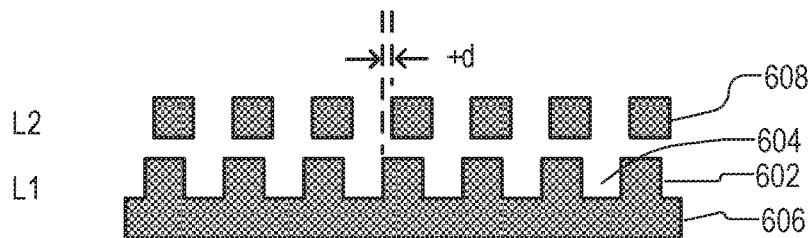
Fig. 7B
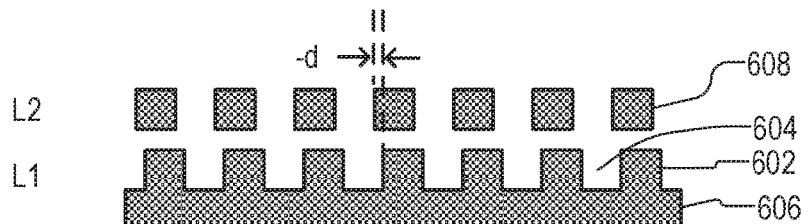
Fig. 7C
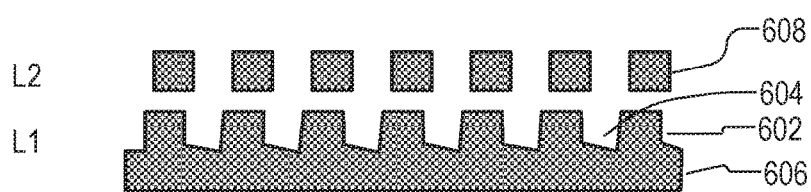
Fig. 7D
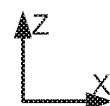

METROLOGY METHOD AND APPARATUS, COMPUTER PROGRAM AND LITHOGRAPHIC SYSTEM

This application incorporates by reference in their entireties U.S. patent application Ser. No. 15/279,860, filed Sep. 29, 2016 and European application 15188190.1, filed Oct. 2, 2015.

BACKGROUND

Field of the Invention

The present invention relates to methods and apparatus for metrology usable, for example, in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

The targets used by conventional scatterometers are relatively large, e.g., 40 μm by 40 μm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 μm by 10 μm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in patent publications US20110027704A, US20110043791A and US20120242970A. The contents of all these applications are also incorporated herein by reference. Diffraction-based overlay using dark-field detection of the diffraction orders enables overlay measurements on smaller targets. These targets can be smaller than the illumination spot and may be surrounded by product structures on a wafer. Targets can comprise multiple gratings which can be measured in one image.

In the known metrology technique, overlay measurement results are obtained by measuring the target twice under certain conditions, while either rotating the target or changing the illumination mode or imaging mode to obtain separately the $-1^{st}$ and the $+1^{st}$ diffraction order intensities. The intensity asymmetry, a comparison of these diffraction order intensities, for a given target provides a measurement of target asymmetry, that is asymmetry in the target. This asymmetry in the target can be used as an indicator of overlay error (undesired misalignment of two layers).

Although the known dark-field image-based overlay measurements are fast and computationally very simple (once calibrated), they rely on an assumption that overlay (i.e., overlay error and deliberate bias) is the only cause of target asymmetry in the target. Any other asymmetry in the target, such as structural asymmetry of features within one or both of the overlaid gratings, also causes an intensity asymmetry in the $1^{st}$ (or other higher) orders. This intensity asymmetry attributable to structural asymmetry, and which is not related to overlay, clearly perturbs the overlay measurement, giving an inaccurate overlay measurement. Asymmetry in the lowermost or bottom grating of a target is a common form of structural asymmetry. It may originate for example in wafer processing steps such as chemical-mechanical polishing (CMP), performed after the bottom grating was originally formed.

Therefore, it is desired to distinguish the contributions to target asymmetry that are caused by overlay error and other effects in a more direct and faster way. It is also desired to simplify the apparatus required for focus and/or aberration measurement within a metrology system. It is further desired to be able to perform critical dimension measurements (and other reconstruction techniques) on small overfilled targets.

SUMMARY OF THE INVENTION

The invention in a first aspect provides a metrology apparatus for measuring a parameter of a lithographic process, the metrology apparatus comprising:

an optical system for measuring a target on a substrate by illuminating the target with measurement radiation and detecting the measurement radiation scattered by the target; and an array of lenses, each lens being operable to focus the scattered measurement radiation onto a sensor, said array of lenses thereby forming an image on the sensor such that said image comprises a plurality of sub-images, each sub-image being formed by a corresponding lens of said array of lenses.

The invention in a further aspect provides a method of measuring a parameter of a lithographic process, comprising measuring a target on a substrate by illuminating the target with measurement radiation and detecting the measurement radiation scattered by the target; forming an image of the target, said image comprising a plurality of sub-images, each sub-image being formed by a corresponding lens of an array of lenses; and measuring said parameter of a lithographic process from said image.

The invention further provides a computer program comprising processor readable instructions which, when run on suitable processor controlled apparatus, cause the processor controlled apparatus to perform the method of the first aspect or the second aspect, and a computer program carrier comprising such a computer program. The processor controlled apparatus may comprise the metrology apparatus of the third aspect or the lithographic system of the fourth aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which:

FIGS. 7A to 7C show schematic cross-sections of overlay gratings having different overlay values in the region of zero;

FIG. 7D is a schematic cross-section of an overlay grating having structural asymmetry in a bottom grating due to processing effects;

DETAILED DESCRIPTION OF EXEMPLARY EMBODIMENTS

Before describing embodiments of the invention in detail, it is instructive to present an example environment in which embodiments of the present invention may be implemented.

Figure 1:
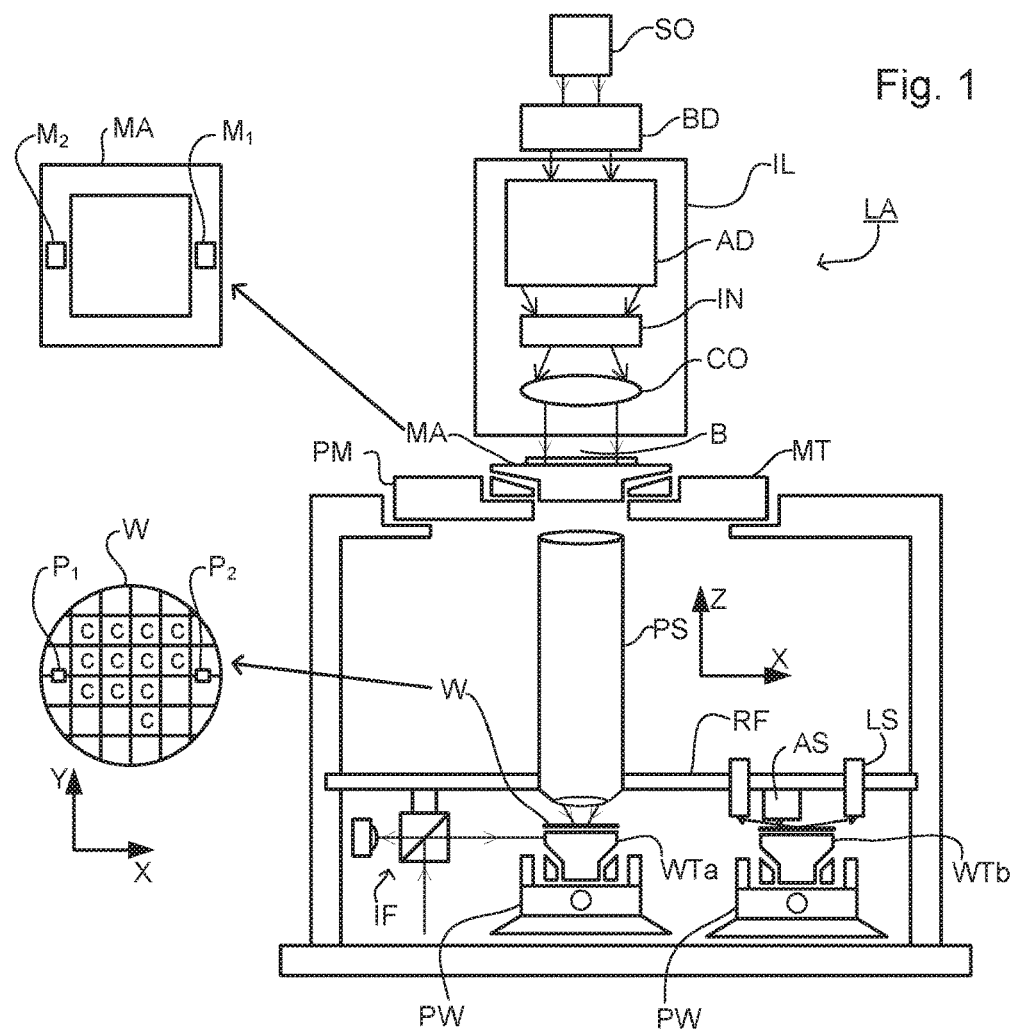
FIG. 1 depicts a lithographic apparatus according to an embodiment of the invention.

FIG. 1 schematically depicts a lithographic apparatus LA. The apparatus includes an illumination optical system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection optical system (e.g., a refractive projection lens system) PS configured to project a pattern imparted to the radiation beam B by patterning device MA onto a target portion C (e.g., including one or more dies) of the substrate W.

The illumination optical system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection optical system PS, which focuses the beam onto a target portion C of the substrate W, thereby projecting an image of the pattern on the target portion C. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

Lithographic apparatus LA in this example is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus.

The depicted apparatus can be used in a variety of modes, including for example a step mode or a scan mode. The construction and operation of lithographic apparatus is well known to those skilled in the art and need not be described further for an understanding of the present invention.

Figure 2:
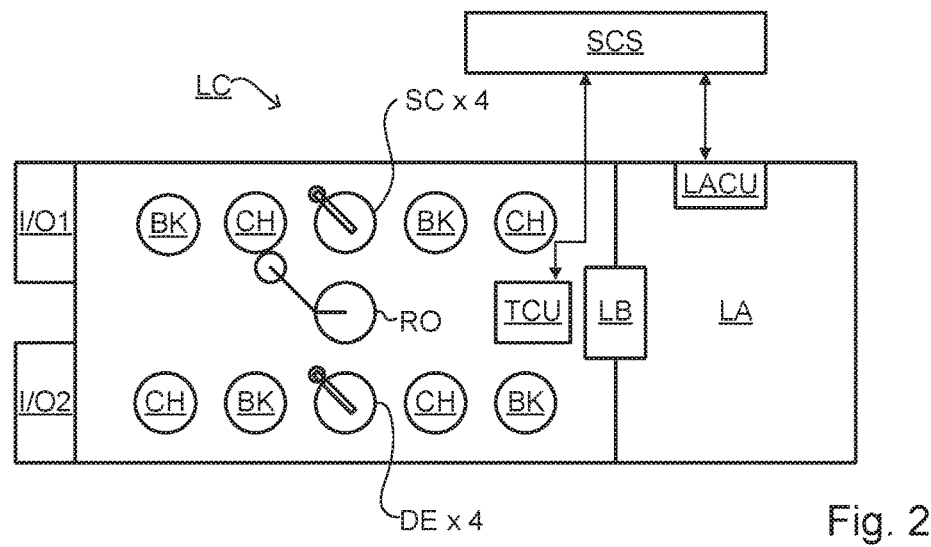
FIG. 2 depicts a lithographic cell or cluster according to an embodiment of the invention.

As shown in FIG. 2, the lithographic apparatus LA forms part of a lithographic system, referred to as a lithographic cell LC or a lithocell or cluster. The lithographic cell LC may also include apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Figure 3A:
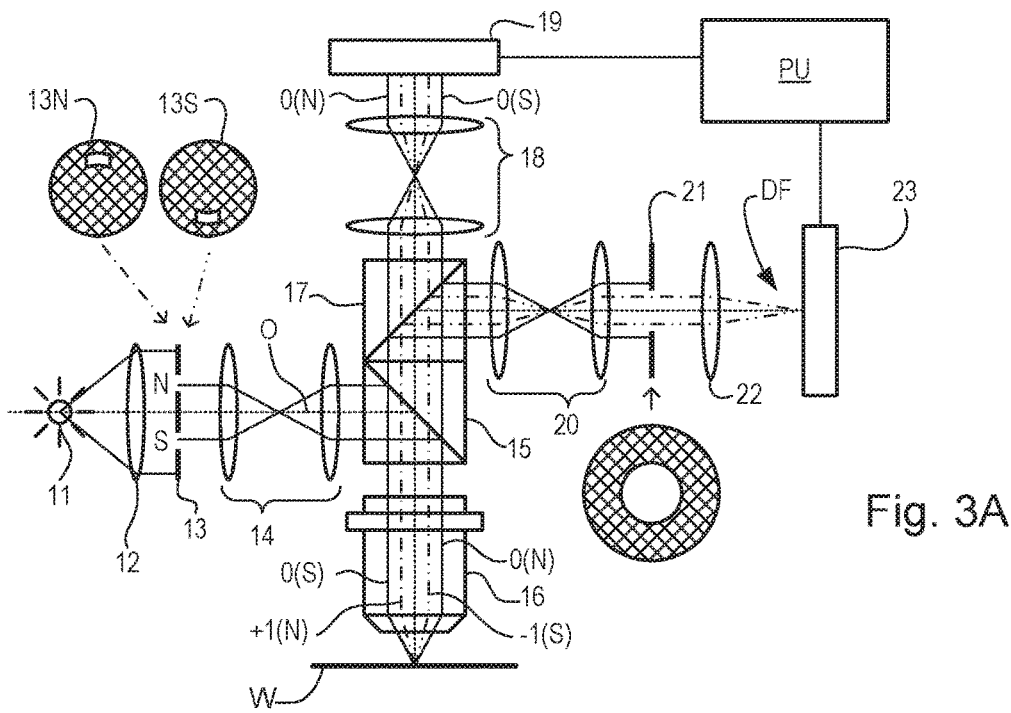
FIGS. 3A-3D comprise 3A a schematic diagram of a dark field scatterometer for use in measuring targets using a first pair of illumination apertures, 3B a detail of diffraction spectrum of a target grating for a given direction of illumination 3C a second pair of illumination apertures providing further illumination modes in using the scatterometer for diffraction based overlay measurements and 3D a third pair of illumination apertures combining the first and second pair of apertures.

A metrology apparatus is shown in FIG. 3(a). A target T and diffracted rays of measurement radiation used to illuminate the target are illustrated in more detail in FIG. 3(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

Figure 3B:
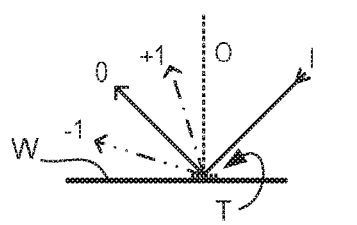

As shown in FIG. 3(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. However, this requirement of a separate branch for focusing is undesirable, increasing cost and complexity. One of the aims of the disclosure removes the need for a separate focusing branch. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 3) can be used in measurements, instead of or in addition to the first order beams.

Figure 3C:
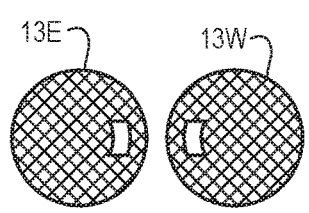

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. Different aperture plates are shown in FIGS. 3(c) and (d). The use of these, and numerous other variations and applications of the apparatus are described in prior published applications, mentioned above.

Figure 4:
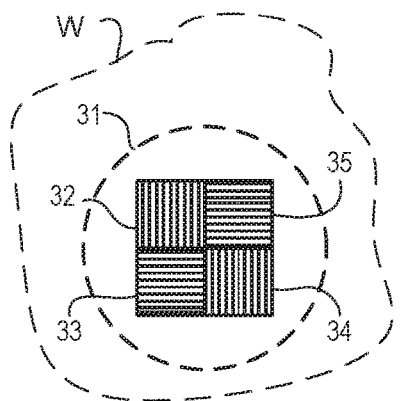
FIG. 4 depicts a known form of multiple grating target and an outline of a measurement spot on a substrate.

FIG. 4 depicts a target or composite target formed on a substrate according to known practice. The target in this example comprises four sub-targets (e.g., gratings) 32 to 35 positioned closely together so that they will all be within a measurement spot 31 formed by the metrology radiation illumination beam of the metrology apparatus. The four targets thus are all simultaneously illuminated and simultaneously imaged on sensors 19 and 23. In an example dedicated to measurement of overlay, gratings 32 to 35 are themselves composite gratings formed by overlying gratings that are patterned in different layers of the semi-conductor device formed on substrate W. Gratings 32 to 35 may have differently biased overlay offsets in order to facilitate measurement of overlay between the layers in which the different parts of the composite gratings are formed. The meaning of overlay bias will be explained below with reference to FIG. 7. Gratings 32 to 35 may also differ in their orientation, as shown, so as to diffract incoming radiation in X and Y directions. In one example, gratings 32 and 34 are X-direction gratings with biases of the +d, −d, respectively. Gratings 33 and 35 are Y-direction gratings with offsets +d and −d respectively. Separate images of these gratings can be identified in the image captured by sensor 23. This is only one example of a target. A target may comprise more or fewer than 4 gratings, or only a single grating.

Figure 3D:
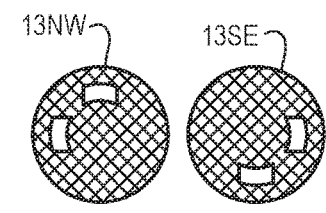
Figure 5:
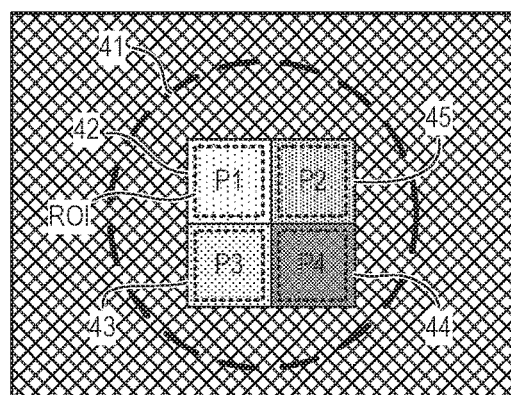
FIG. 5 depicts an image of the target of FIG. 4 obtained in the scatterometer of FIG. 3.

FIG. 5 shows an example of an image that may be formed on and detected by the sensor 23, using the target of FIG. 4 in the apparatus of FIG. 3, using the aperture plates 13NW or 13SE from FIG. 3(d). While the pupil plane image sensor 19 cannot resolve the different individual gratings 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target gratings 32 to 35. If the targets are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole.

Once the separate images of the targets have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

One downside of such images is that no angle resolved information can be obtained from the image, only an averaged (or summed) intensity value. This means, for example, that it is not possible to measure overlay as a function of angle. Only a single overlay value can be obtained, from which it is not possible to distinguish actual overlay from intensity asymmetry resultant from structural asymmetry of the target.

Figure 6:
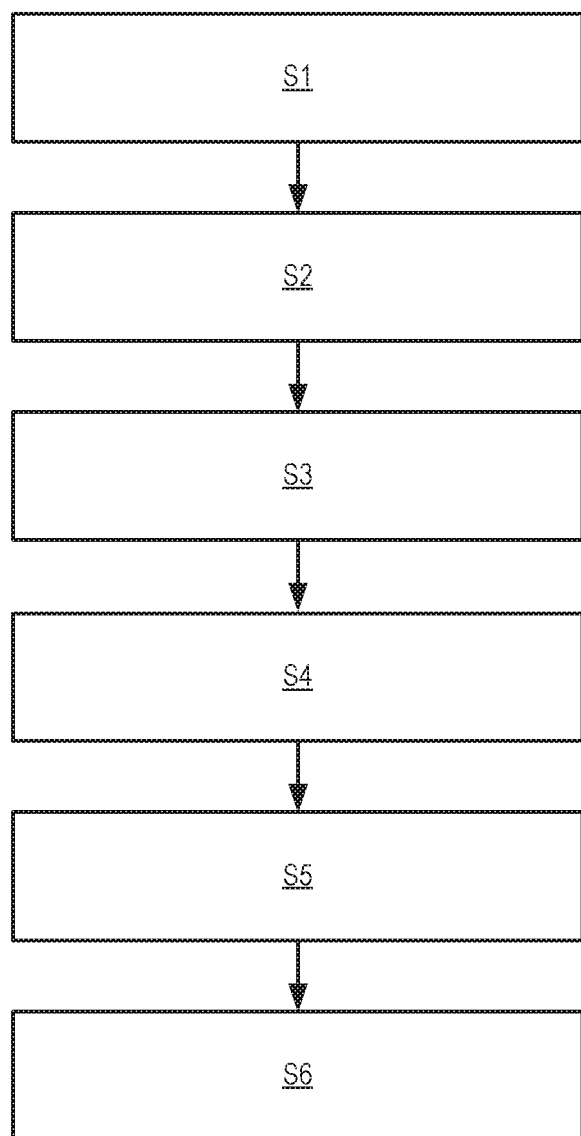
FIG. 6 is a flowchart showing the steps of an overlay measurement method using the scatterometer of FIG. 3 and adaptable to form embodiments of the present invention.

FIG. 6 illustrates how, using for example the method described in application WO 2011/012624, overlay error (i.e., undesired and unintentional overlay misalignment) between the two layers containing the component targets 32 to 35 is measured. Such a method may be referred to a micro diffraction based overlay (DBO). This measurement is done through target asymmetry, as revealed by comparing their intensities in the +1 order and −1 order dark field images (the intensities of other corresponding higher orders can be compared, e.g. +2 and −2 orders) to obtain a measure of the intensity asymmetry. At step S1, the substrate, for example a semiconductor wafer, is processed through a lithographic apparatus, such as the lithographic cell of FIG. 2, one or more times, to create a target including the gratings 32-35. At S2, using the metrology apparatus of FIG. 3 or FIG. 10, an image of the targets 32 to 35 is obtained using only one of the first order diffracted beams (say −1). At step S3, whether by changing the illumination mode, or changing the imaging mode, or by rotating substrate W by 180° in the field of view of the metrology apparatus, a second image of the targets using the other first order diffracted beam (+1) can be obtained. Consequently the +1 diffracted radiation is captured in the second image. By using prisms to separate the orders, separated images of the target formed by both +1 and −1 diffracted beams (and possibly also the zeroth order) can be obtained in a single capture.

Note that, by including only half of the first order diffracted radiation in each image, the 'images' referred to here are not conventional dark field microscopy images. The individual target lines of the targets will not be resolved. Each target will be represented simply by an area of a certain intensity level. In step S4, a region of interest (ROI) is identified within the image of each component target, from which intensity levels will be measured.

Having identified the ROI for each individual target and measured its intensity, the asymmetry of the target, and hence overlay error, can then be determined. This is done (e.g., by the processor PU) in step S5 comparing the intensity values obtained for +1 and −1 orders for each target 32-35 to identify their intensity asymmetry, e.g., any difference in their intensity. The term "difference" is not intended to refer only to subtraction. Differences may be calculated in ratio form. In step S6 the measured intensity asymmetries for a number of targets are used, together with knowledge of any known imposed overlay biases of those targets, to calculate one or more performance parameters of the lithographic process in the vicinity of the target T. In the applications described herein, measurements using two or more different measurement recipes will be included. A performance parameter of great interest is overlay. As will be described later, the novel methods also allow other parameters of performance of the lithographic process to be calculated. These can be fed back for improvement of the lithographic process, and/or used to improve the measurement and calculation process of FIG. 6 itself.

In the prior applications, mentioned above, various techniques are disclosed for improving the quality of overlay measurements using the basic method mentioned above. These techniques will not be explained here in further detail. They may be used in combination with the techniques newly disclosed in the present application, which will now be described.

FIG. 7 shows schematic cross sections of targets (overlay gratings), with different biases. These can be used as the target T on substrate W, as seen in FIGS. 3 and 4. Gratings with periodicity in the X direction are shown for the sake of example only. Different combinations of these gratings with different biases and with different orientations can be provided separately or as part of a target.

Starting with FIG. 7(a) a target 600 formed in two layers, labeled L1 and L2, is shown. In the lowermost or bottom layer L1, a first structure (the lowermost or bottom structure), for example a grating, is formed by features 602 and spaces 604 on a substrate 606. In layer L2 a second structure, for example a grating, is formed by features 608 and spaces 610. (The cross-section is drawn such that the features 602, 608 (e.g., lines) extend into the page.) The grating pattern repeats with a pitch P in both layers. Features 602 and 608 may take the form of lines, dots, blocks and via holes. In the situation shown at (a), there is no overlay contribution due to misalignment, e.g., no overlay error and no imposed bias, so that each feature 608 lies exactly over a feature 602 in the first structure.

At FIG. 7(b), the same target with a first known imposed bias +d is shown, such that the features 608 of the first structure are shifted by a distance d to the right, relative to the features of the second structure. The bias distance d might be a few nanometers in practice, for example 10 nm-20 nm, while the pitch P is for example in the range 300-1000 nm, for example 500 nm or 600 nm. At FIG. 7(c) we see another feature with a second known imposed bias −d, such that the features of 608 are shifted to the left. Biased targets of this type shown at (a) to (c) are well known in the art, and used in the prior applications mentioned above.

FIG. 7(d) shows schematically a phenomenon of structural asymmetry, in this case structural asymmetry in the first structure (bottom grating asymmetry). The features in the gratings at (a) to (c), are shown as perfectly square-sided, when a real feature would have some slope on the side, and a certain roughness. Nevertheless they are intended to be at least symmetrical in profile. The features 602 and/or spaces 604 at (d) in the first structure no longer have a symmetrical form at all, but rather have become distorted by processing steps. Thus, for example, a bottom surface of each space has become tilted. Side wall angles of the features and spaces have become asymmetrical also. As a result of this, the overall target asymmetry of a target will comprise an overlay contribution independent of structural asymmetry (i.e., an overlay contribution due to misalignment of the first structure and second structure; itself comprised of overlay error and any known imposed bias) and a structural contribution due to this structural asymmetry in the target.

When overlay is measured by the method of FIG. 6 using only two biased gratings, the process-induced structural asymmetry cannot be distinguished from the overlay contribution due to misalignment, and overlay measurements (in particular to measure the undesired overlay error) become unreliable as a result. Structural asymmetry in the first structure (bottom grating) of a target is a common form of structural asymmetry. It may originate, for example, in the substrate processing steps such as chemical-mechanical polishing (CMP), performed after the first structure was originally formed.

In WO 2013/143814 A1, it is proposed to use of three or more component targets to measure overlay by a modified version of the method of FIG. 6. Using three or more targets of the type shown in FIGS. 7(a) to (c) are used to obtain overlay measurements that are to some extent corrected for structural asymmetry in the target gratings, such as is caused by bottom grating asymmetry in a practical lithographic process. However, this method requires a new target design (e.g. different to that illustrated in FIG. 4) and therefore a new reticle will be required. Furthermore, the target area is larger and therefore consumes more substrate area.

Figure 8:
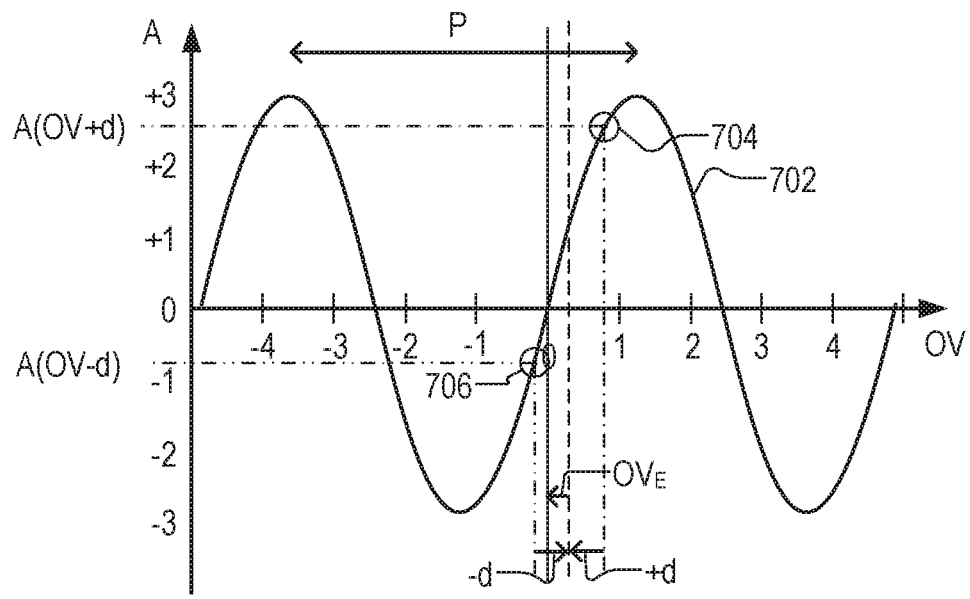
FIG. 8 illustrates known principles of overlay measurement in an ideal target, not subject to structural asymmetry.
Figure 9:
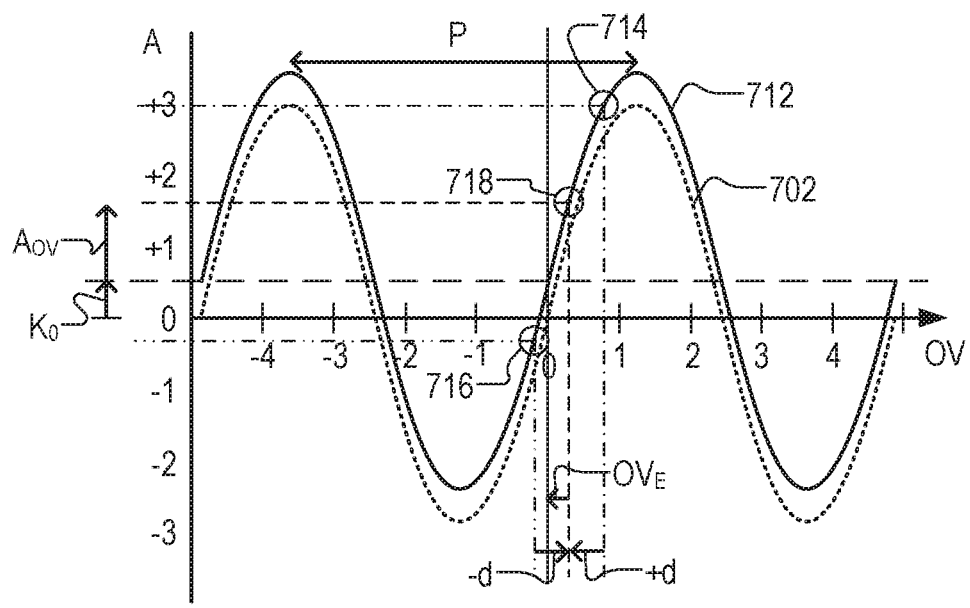
FIG. 9 illustrates a principle of overlay measurement in a non-ideal target, with correction of structural asymmetry as disclosed in embodiments of the invention.

In FIG. 8 a curve 702 illustrates the relationship between overlay OV and intensity asymmetry A for an 'ideal' target having zero offset and no structural asymmetry within the individual gratings forming the target. Consequently, the target asymmetry of this ideal target comprises only an overlay contribution due to misalignment of the first structure and second structure resultant from a known imposed bias and overlay error $OV_E$. This graph, and the graph of FIG. 9, is to illustrate the principles behind the disclosure only, and in each graph, the units of intensity asymmetry A and overlay OV are arbitrary. Examples of actual dimensions will be given further below.

In the 'ideal' situation of FIG. 8, the curve 702 indicates that the intensity asymmetry A has a non-linear periodic relationship (e.g., sinusoidal relationship) with the overlay. The period P of the sinusoidal variation corresponds to the period or pitch P of the gratings, converted of course to an appropriate scale. The sinusoidal form is pure in this example, but can include harmonics in real circumstances.

As mentioned above, biased gratings (having a known imposed overlay bias) can be used to measure overlay, rather than relying on a single measurement. This bias has a known value defined in the patterning device (e.g. a reticle) from which it was made, that serves as an on-wafer calibration of the overlay corresponding to the measured intensity asymmetry. In the drawing, the calculation is illustrated graphically. In steps S1-S5, intensity asymmetry measurements $A^{+d}$ and $A^{-d}$ are obtained for targets having imposed biases +d an –d respectively (as shown in FIGS. 7 (b) and (c), for example). Fitting these measurements to the sinusoidal curve gives points 704 and 706 as shown. Knowing the biases, the true overlay error $OV_E$ can be calculated. The pitch P of the sinusoidal curve is known from the design of the target. The vertical scale of the curve 702 is not known to start with, but is an unknown factor which can be referred to as a $1^{st}$ harmonic proportionality constant, $K_1$. This constant $K_1$ is a measure of the sensitivity of the intensity asymmetry measurements to the target.

In equation terms, the relationship between overlay error $OV_E$ and intensity asymmetry A is assumed to be:

$$A_{\pm d} = \frac{2\pi}{P} K_1 \sin(OV_E \pm d) \quad (1)$$

where overlay is expressed on a scale such that the target pitch P corresponds to an angle $2\pi$ radians.

As overlay is very small, this relationship can be approximated to a linear relationship over the range of interest, using the assumption $\sin(OV_E \pm d) = OV_E \pm d$:

$$A_{\pm d} \approx \frac{2\pi}{P} K_1 (OV_E \pm d) \quad (2)$$

Using two measurements of targets with different, known biases (e.g. +d and –d) the overlay error $OV_E$ can be calculated.

FIG. 9 shows a first effect of introducing structural asymmetry, for example the bottom grating asymmetry illustrated in FIG. 7(d). The 'ideal' sinusoidal curve 702 no longer applies. However, at least approximately, bottom grating asymmetry or other structural asymmetry has the effect of adding an offset term to the intensity asymmetry A, which is relatively constant across all overlay values. The resulting curve is shown as 712 in the diagram, with label $K_0$ indicating the offset term due to structural asymmetry. Offset term $K_0$ is dependent upon a selected characteristic of the measurement radiation, such as the wavelength and polarization of the measurement radiation (the "measurement recipe"), and is sensitive to process variations. In equation terms, the relationship used for calculation in step S6 becomes:

$$A_{\pm d} = K_0 + \frac{2\pi}{P} K_1 \sin(OV_E \pm d) \approx K_0 + \frac{2\pi}{P} K_1 (OV_E \pm d) \quad (3)$$

the above approximation again being valid for the overlay range of interest.

Where there is structural asymmetry, the overlay model described by Equation (2) will provide overlay error values which are impacted by the offset term $K_0$, and will be inaccurate as a consequence. The structural asymmetry will also result in differences in measurements of the same target using different measurement recipes, when mapping the overlay error, because the intensity shift described by the offset term is wavelength dependent. At present there is no method to remove the overlay contribution due to structural asymmetry in a single measurement step, thereby correcting the overlay error measurements. Therefore, a throughput penalty is incurred to correct for the offset term $K_0$, or slight changes in substrate processing will lead to overlay variation, thereby impacting the overlay control loop APC (Automatic Process Control) and the device yield.

It is proposed to measure the target asymmetry of a target, and therefore overlay which does not neglect the effect of the structural asymmetry, while allowing the use of current target designs such as those illustrated in FIG. 4. This modelling may be performed as a modification to step S6 in the method illustrated in FIG. 6. The method proposed can calculate overlay errors accurately using real substrate measurement data, and which can determine the optimal or preferred combination of targets and measurement recipes. No simulation or reconstruction is needed.

It is therefore proposed to add an array of lenses, which may be a microlens array, into the pupil plane of the second measurement branch of the arrangement of FIG. 3(a). In an embodiment this may be at or near the focal plane of the output lens assembly 20 defined by its focal length $f_{20}$. This provides a number of advantages over the previous arrangements described. Each microlens of the microlens array creates an individual image or sub-image from a localized section of the pupil. From the local sub-image, a local overlay calculation can be performed. The positions of the sub-images provide an aberration distribution over the exit pupil. This aberration distribution allows correction to be made for the aberration, and also allows focus to be determined. This determination of focus within the second measurement branch (that used for performing μDBO measurements) means that the first measurement branch as depicted in FIG. 3(a) may be dispensed with.

The resultant plenoptic image can be thought of as a hybrid image comprising both image plane information (the sub-images) and the wavefront distortion information (from the relative positions of the sub-images). Additionally, the intensities of the sub-images allow a pupil image to be calculated which is free from the influence of structural asymmetry of from product structure. Such a pupil image can be constructed from the relative intensities of the sub-images comprised within an image. The pupil image can be used for reconstructing structural asymmetry and for performing CD metrology on small (finite) targets.

Figure 10:
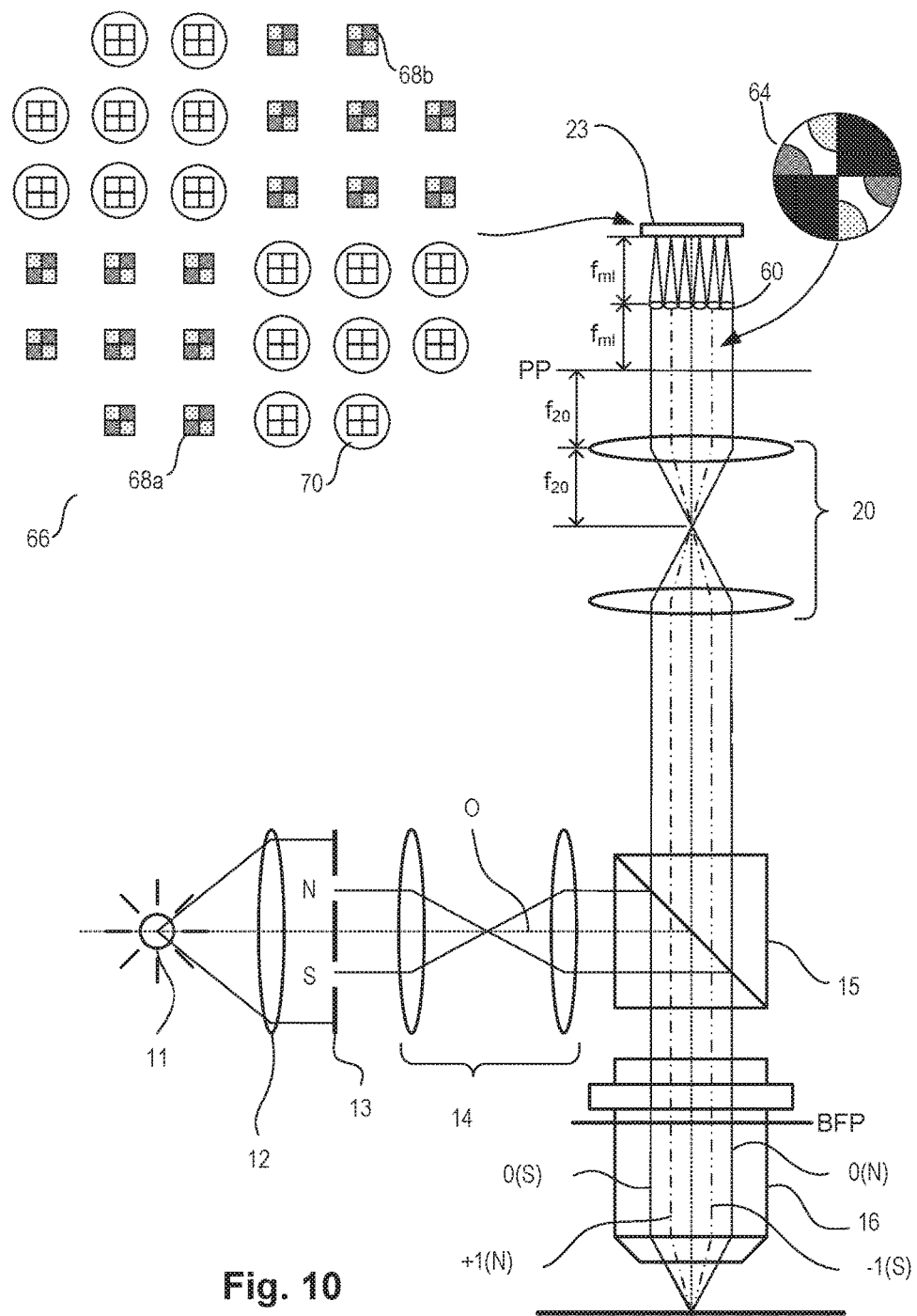
FIG. 10 is a schematic diagram of a dark field scatterometer according to an embodiment of the invention.

FIG. 10 shows a metrology apparatus suitable for performing overlay measurements. It is largely similar to the metrology apparatus shown in FIG. 3(a), but only comprising a single measurement branch, equivalent to the second measurement branch of FIG. 3(a), such that the sensor 23 is in the image plane. The elements common with the metrology apparatus shown in FIG. 3(a) will not be described further.

A microlens array 60 is located between the pupil plane PP of the optical system, and the image plane (sensor 23). The term 'pupil plane' in this context refers to any plane in the optical system which is an image of the 'Back focal plane' BFP of the objective lens 16. The output lens assembly 20 creates an image of the back focal plane BFP of the objective lens 16. The microlens array 60 may comprise a 2 dimensional array of individual lenses (or microlenses). The microlens array 60 may be such that it is located at the pupil plane PP (or more specifically at the focal plane of the output lens 20). Alternatively, the microlens array 60 may be located at a distance $f_{ml}$ from both the pupil plane PP and the image plane, where distance $f_{ml}$ is the focal length of each microlens within the microlens array (assuming all microlenses in the array are similar). In practice, it may be preferred to place the microlens array at the exact focal plane of the output lens 20 in order to minimize vignetting, although it may be more convenient to place the microlens array forward of this, such that the transform relation is unencumbered with quadratic phase factors; for example in the location shown in FIG. 10 at a distance from the pupil plane equal to the focal length $f_{ml}$ of each microlens of the microlens array.

Each microlens produces a focused image on the sensor 23. The microlens array 60 replaces the final lens 22 and any prisms (not shown) of the metrology apparatus shown in FIG. 3(a). In this configuration, the apparatus is similar to a Shack-Hartmann sensor. The radiation profile at exit pupil 64 is imaged by the microlens array 60 onto sensor 23, resulting in a plenoptic image 66 comprising sub-images 68a, 68b 70, each created by one microlens of the microlens array 60. Higher order sub-images 68a are formed from one of the first orders of scattered radiation, higher order sub-images 68b are formed from the other of the first orders of scattered radiation, and zeroth order sub-images 70 are formed from the zeroth order of scattered radiation. Higher order sub-images 68a and 68b may also comprise images formed from orders higher than the first order. The zeroth order sub-images 70 may be attenuated by an absorbing neutral density filter so that they are within the dynamic range of the sensor or a high dynamic range detector may be used. Alternatively, the zeroth order may be blocked altogether.

A local overlay from each sub-image 68a, 68b can be calculated. This can be done using known μDBO processing techniques such as those already described (e.g., from intensity asymmetries from biased gratings). However, as will be described below, these local values may be combined to obtain an overall overlay value. The combination may include a weighting of the local overlay values.

Where the imaging is ideal, with no aberrations (for example, defocus aberration or aberration introduced by the imaging system), the sub-images 68a, 68b, 70 will lie on a uniform 2D grid. This assumes that the microlenses are arranged in a uniform 2D grid in the microlens array 60. Should there be any aberration, this will manifest itself in terms of a wavefront curvature (phase distribution offsets). The microlens array 60 allows measurement of this wavefront curvature, this can be done by measuring the deviation of the positions of the sub-images 68a, 68b, 70 relative to a uniform grid (grid distortion). From this grid distortion, it can be determined which part of the pupil has the most distortion, and therefore which is most sensitive to aberration. Weighting can then be applied over the pupil depending on which parts of the pupil are the most process dependent. This can be simulated in advance from a sensor model when the type of target being used is known. The most process dependent parts of the pupil can also be inferred from measurements, for example, by looking at parts of the pupil which have a relatively higher intensity.

This measured aberration can be further decomposed into aberration resulting from defocus and aberration resulting from other sources (lens aberrations, other imaging aberrations etc.). This is because the grid distortion measured from plenoptic image 66 which results from non-focus aberrations tends to be static for different degrees of defocus, while the grid distortion due to defocus will vary with (de)focus. By correcting out the grid distortions resultant from non-focus aberrations, correct focus can be inferred from the plenoptic image 66 as that corresponding to there being no grid distortion in plenoptic image 66. Defocus of the plenoptic image in a first direction will result in distortion from a grid in a first direction (e.g., radially outwards with respect to the grid center). Similarly, defocus of the plenoptic image in a second direction will result in distortion from a grid in a second direction (e.g., radially inwards with respect to the grid center).

The grid distortion which results from non-focus aberrations may be corrected for by performing initial calibration measurements, this may comprise obtaining plenoptic images 66 at two or more set degrees of defocus, and calculating the static grid distortion in these measurements. Such calibration also allows, where the plenoptic image is defocussed, the degree of defocus to be measured.

While the above methodology is described mainly in terms of defocus, it may be used for any aberration. Any aberration over the pupil can be detected and an aberration free, angularly resolved measurement for overlay can be obtained. Smoothly varying aberrations can be thought of as piecewise linear. Importantly, it is observed that the aberrations only cause the sub-images 68a, 68b. 70 to deviate from the grid; they do not change the local overlay measurements.

It is as a result of this ability to measure aberrations, and in particular focus, that an additional measurement branch is not necessarily required. The single measurement branch can be used to obtain overlay measurements of small compound targets (unresolvable in a pupil image) by measuring intensity asymmetry in images of the targets using μDBO techniques. The single measurement branch can also be used to determine whether the objective lens 16 is correctly focused on the substrate. The single measurement branch may further enable correction of focus and/or non-focus aberrations obtained from pupil perturbations derived from the measured grid distortions.

Figure 11:
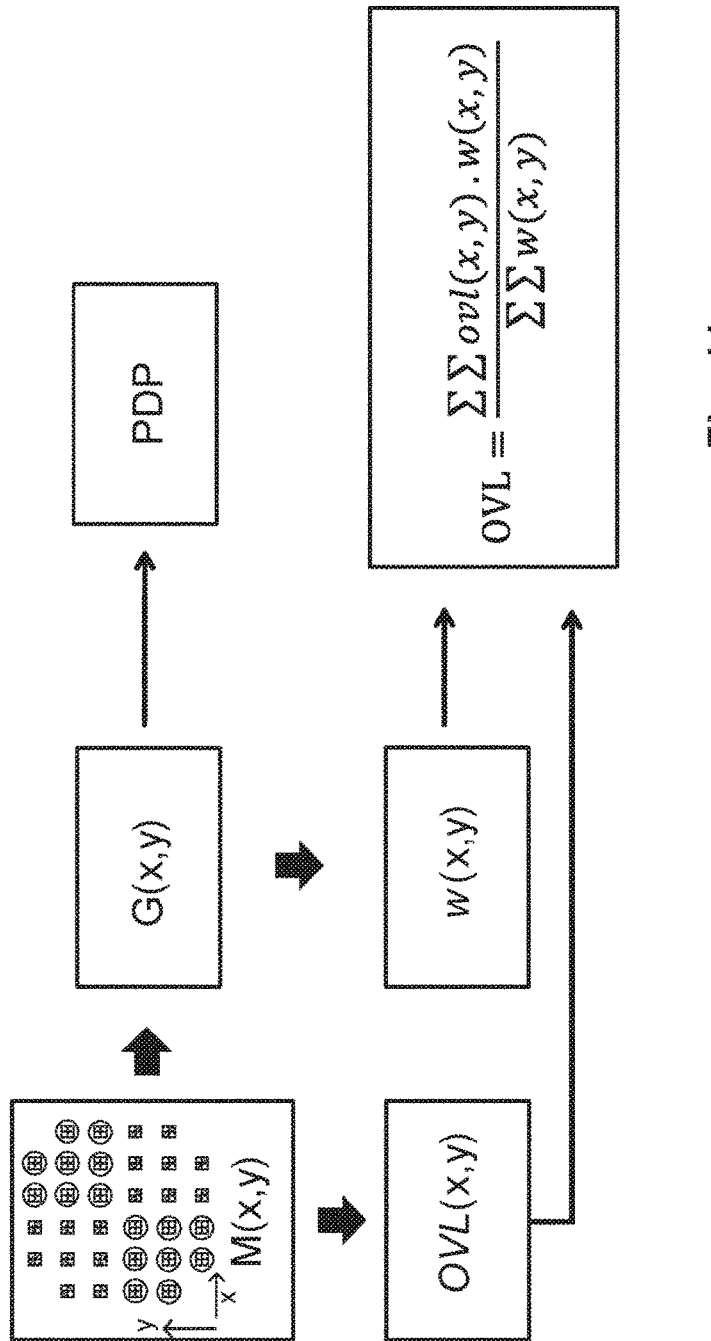
FIG. 11 is a flowchart of the steps of a method according to an exemplary embodiment of the invention.

FIG. 11 is a flow diagram illustrating a method of performing overlay measurements, including calibration according to the methods disclosed. In a calibration stage, a weighting w(x,y) may be determined. In a first step, measured data M(x,y) is obtained, comprising a raw plenoptic image made up of a number of sub-images arranged in a two dimensional array (x,y). From each of these sub-images, a local overlay value OVL(x,y) and a local measure of the grid distortion G(x,y) is determined. These steps may be repeated for a number of targets on a substrate, and ideally for all targets on a substrate. Furthermore, this may be done for a plurality of substrates (e.g., substrates corresponding to the same stack). As a result, the grid distortion G(x,y) may be determined for every position on a substrate and for a plurality of substrates. Variance of the grid distortion G(x,y) dataset can be used to determine a weighting w(x,y) for the local overlay values OVL (x,y) in terms of pupil position (x,y). The weighting w(x,y) may also be determined by a prior digital computation with knowledge of the target layout. By way of example, the weighting may be determined using a heatmap created from the variance in grid distortion G(x,y). This heatmap may show distortion in terms of pupil position. Therefore, the heatmap will indicate which areas of the pupil display the greatest distortion, and are most process dependent and sensitive to aberrations. These areas may have a lower weighting assigned thereto. In some cases the lower weighting may be a zero weighting, such that local overlay values from the corresponding pupil area will be ignored when calculating an overall value. The weighting may be binary, such that areas of low distortion (e.g., below a threshold) are weighted at 100% and areas of high distortion (e.g., above a threshold) are weighted at 0%. Or else the weighting may be of greater resolution, or continuous.

Additionally, the calibration stage may comprise determining machine constants and process dependent parameters PDP from the grid distortion G(x,y).

Once the calibration stage is completed, the weighting can be used to obtain an overall overlay measurement value from a set of local overlay values obtained from a plenoptic image. This can be done for all the overlay values OVL(x,y) obtained from the measurement data M(x,y) during the calibration phase. The weighting w(x,y) can also be applied to any subsequent measurements. The measurement data M(x,y) will comprise a plenoptic image comprising plural (higher order) sub-images 68a, 68b, as before. Local overlay is calculated OVL(x,y) and the local overlay values combined into a single overall overlay value OVL in accordance with the weighting w(x,y). In a specific embodiment, the combination may be as follows:

$$OVL = \frac{\sum\sum ovl(x, y) \cdot w(x, y)}{\sum\sum w(x, y)} \quad (4)$$

A further advantage of the apparatus of FIG. 10, is that it enables an overlay value to be obtained from a single µDBO measurement, using only a single measurement radiation wavelength and/or polarization. This allows for correction for structural asymmetry (e.g., bottom grating asymmetry) within the measured target.

By filtering out the influence of the product structure, the overlay can be measured independently with difference angles of incidence of the measurement radiation on the target. Since true overlay is independent of the angle of incidence, while any offset introduced by structural asymmetry within the target is dependent upon angle of incidence, it is possible to separate the measured overlay into true overlay and that caused by structural asymmetry.

A known µDBO technique may comprise obtaining in a single measurement, images of a target, such as that illustrated in FIG. 5, for both +1 and −1 orders. The +1 and −1 orders (and optionally the zeroth order) may be separated by prisms in the pupil plane, such that each image is separate on the sensor. As already described, the target may comprise one or more pairs of gratings having two different offsets, for example +d and −d. As a result, a single measurement of a target can yield sufficient information to cancel for $K_1$ in Equation (1) or (2), enabling the overlay error $OV_E$ to be determined assuming no structural asymmetry. However such a measurement will not yield sufficient information to also cancel, or obtain a value for, $K_0$ when there is structural asymmetry (as there always will be) and Equation (3) applies. Therefore, more measurements are required with, for example, measurement radiation of a different wavelength.

Using the metrology apparatus of FIG. 10, the resultant plenoptic image 66 may comprise multiple pairs of individual higher order sub-images 68a, 68b of the target (comprising gratings having two offsets), with each pair of sub-images comprising a sub-image obtained using +1 radiation and a sub-image obtained using −1 radiation. Each pair of sub-images will correspond to a different angle of incidence. Consequently, a single measurement may yield sufficient information to obtain a value for the offset $K_0$ and to cancel for $K_1$, meaning that Equation (3) can be solved for the overlay error $OV_E$.

Clearly, there are a number of ways of solving for $K_0$ and determining overlay error $OV_E$, using the general methods disclosed herein. In an embodiment, values of asymmetry measurements $A^{+d}$ are plotted against the determined values of asymmetry measurements $A^{-d}$, obtained for targets having imposed biases +d an −d respectively. Each point on the plot corresponds to a pair of sub-images. The offset $K_0$ can be found from the intersects with each axis, of a line fitted to these points, the line being described by:

$$\frac{A^{+d} - K_0}{A^{-d} - K_0} = \frac{OV_E + d}{OV_E - d} \quad (5)$$

The fact that the single plenoptic image provides sufficient points (i.e., two but preferably more) to plot a line enables this method to be used while also enabling the axes intersects to be found. By contrast, using a conventional image yields only a single point, and an assumption needs to be made that the line passes through the origin (i.e., there is no structural asymmetry). Alternatively, more than one measurement is made, decreasing throughput.

Another advantage of the apparatus of FIG. 10 is that it enables better asymmetry calibration as it provides robustness to the cross term between process asymmetry and sensor induced asymmetry. Because the pupil is resolved using the apparatus of FIG. 10, it is possible to also determine asymmetry in the entrance pupil. This may be as a result of a phase aberration in the metrology system optics, which can be seen in the resolved pupil. Consider a plane wave incident on the target. In a scalar approximation, the scalar field reflected by the target at a 2D plane parallel to the target can be represented as $$r(x,y)=a(x,y)e^{i\varphi(x,y)} \quad (6)$$

Where r(x,y) is the reflected field comprising of an amplitude distribution, a(x,y) and a phase distribution φ(x,y). If the target is a an overlay grating, the reflected field has an asymmetry manifested in the amplitude term a(x,y). This scalar field propagates through the sensor's optics and is detected at a 2D intensity detector.

The scalar field at a pupil plane in the sensor is given by a scaled Fourier transform of this field which is the action of a lens on an input field in the scalar approximation. The field at the pupil plane can be described as $$\tilde{r}(k_x,k_y)=\tilde{a}(k_x,k_y)e^{i\tilde{\varphi}(k_x,k_y)} \quad (7)$$

Where $\tilde{r}(k_x,k_y)$ represents the scaled Fourier transform of the input scalar field.

Sensor aberrations largely manifest themselves as phase distributions in the pupil plane. For example, a defocus can be described as a quadratic phase distribution over the pupil and a tilt can be described as a linear phase distribution in the corresponding direction.

In this case, the scalar field the aberrated pupil plane can be described as $$\tilde{r}'(k_x,k_y)=\tilde{a}(k_x,k_y)e^{i\tilde{\varphi}(k_x,k_y)}e^{i\varepsilon(k_x,k_y)} \quad (8)$$

Where $e^{i\varepsilon(k_x,k_y)}$ is the phase aberration.

If the overlay is measured in the pupil plane, i.e, if the 2D detector is placed in the pupil plane, then the intensity recorded is $$I_p(k_x,k_y)=|\tilde{r}'(k_x,k_y)|^2=|\tilde{a}(k_x,k_y)e^{i\tilde{\varphi}(k_x,k_y)}e^{i\varepsilon(k_x,k_y)}|^2=|\tilde{a}(k_x,k_y)|^2 \quad (9)$$

The pupil plane phase aberration does not impact the overlay measurement.

If however, the overlay is measured in the field plane. The distribution in the field plane is given by a scaled Fourier transform of the pupil plane distribution.

$$a'(x,y) = \int\int_{-k}^{k} \tilde{a}(k_x,k_y)e^{i\tilde{\varphi}(k_x,k_y)}e^{i\varepsilon(k_x,k_y)}e^{i\frac{2\pi}{\lambda f}(k_x x+k_y y)}dk_x dk_y \quad (10)$$

$$I_f(x,y) =$$

$$|a'(x,y)|^2 = \left|\int\int_{-k}^{k} \tilde{a}(k_x,k_y)e^{i\tilde{\varphi}(k_x,k_y)}e^{i\varepsilon(k_x,k_y)}e^{i\frac{2\pi}{\lambda f}(k_x x+k_y y)}dk_x dk_y\right|^2$$

The detected signal is the modulus square of the complex distribution. It can be seen that due to the Fourier transform operation, the sensor induced aberration $e^{i\varepsilon(k_x,k_y)}$ couples completely into the detected signal. Every detected pixel in $I_f(x,y)$ experiences contribution from the full pupil and the image is distorted by the sensor aberration.

This can also be seen via the convolution theorem. The Fourier transform of a multiplication can be expressed as a convolution of the individual Fourier transforms.

$$a'(x,y) = \int\int_{-k}^{k} \tilde{a}(k_x,k_y)e^{i\tilde{\varphi}(k_x,k_y)}e^{i\varepsilon(k_x,k_y)}e^{i\frac{2\pi}{\lambda f}(k_x x+k_y y)}dk_x dk_y \quad (11)$$

$$= a(x,y) \otimes \int\int_{-k}^{k} e^{i\varepsilon(k_x,k_y)}e^{i\frac{2\pi}{\lambda f}(k_x x+k_y y)}dk_x dk_y$$

$$= a(x,y) \otimes \tilde{\varepsilon}(x,y)$$

Where $\tilde{\varepsilon}(x,y)$ is the Fourier transform of the aberration function. It can be seen that the complex distribution in the field plane is convolved by the Fourier transform of the pupil aberration function and as a result is 'blurred' by the sensor aberrations. For example, if the sensor aberration is due to a defocus, the image gets a defocus blur. Thus the image in the field plane is distorted and is more prone to focus errors than the image of the pupil plane.

The apparatus of FIG. 10 allows thick stacks to be imaged, due to the increased depth of focus of each microlens. This is in contrast to grating images of thick stacks (e.g., 3D NAND) which show tilts when measured off-axis (e.g., with prisms). These tilts depend on focus and therefore stack thickness between the bottom and top grating.

The apparatus of FIG. 10 allows measurement of multi-target marks in a single measurement. Multi-target marks comprise targets having gratings in different layer combinations in a single mark; for example a mark may comprise a target comprising gratings in layer 1 and layer 2 and a target comprising gratings in layer 1 and layer 3. This allows measurement of overlay between different layer combinations in a single measurement. Each of these targets may have different pitches. The area of the pupil which corresponds to a particular target depends on the pitch, and therefore the different targets may be resolved within the pupil. As a result, different sub-images will correspond to different targets, and therefore overlay for different layer combinations can be obtained in a single measurement.

For relatively larger pitches, higher diffracted orders are also present in the exit pupil plane. The overlay of larger pitch structures may be obtained from a combination of many such sub-images, using sub-images appropriately selected from both the 1$^{st}$ order and the higher orders. At the same time, a different set of sub-images may be chosen for the overlay measurement of the target with a smaller pitch. For example, a multi-target overlay mark may have two different pitches, P1 and P2, such that P1 is a large pitch for which a higher order is detected within the pupil in addition to the first order and P2 is a smaller pitch for which only the first order is detected at the edge of the pupil. The sub-images formed due to diffraction from the P1 target arise in two different regions of the pupil, whereas the sub-images from the P2 target are formed at the edge of the exit pupil. For an overlay measurement of the P1 target, a different set of images may be chosen and with different weighting than for an overlay measurement of the P2 target. Consequently, using the plenoptic image, it becomes possible to mix and weight different sub-images for each grating in a multi-target mark.

The apparatus of FIG. 10 may also be used for CD (critical dimension) reconstruction, and in particular CD reconstruction of small targets. CD reconstruction is normally done in the first measurement branch of the apparatus of FIG. 3(a) as it requires a diffraction spectrum (pupil image) to be obtained and one or more profile parameters of a target inferred from the pupil image using reconstruction techniques. Such reconstruction techniques may comprise iteratively adjusting a candidate profile parameter, modelling the resultant pupil image and comparing this to the measured pupil image. This is repeated until the modelled and measured pupil images converge. Reconstruction techniques may also comprise (in addition or as an alternative) comparing the pupil image to a library of previous calculated pupil images corresponding to known profile parameters until a closest match is found. Because CD reconstruction requires a pupil image, imaging techniques have not been possible, and therefore it has not been possible to use small, overfilled targets which are smaller than the measurement spot. If overfilled targets were to be used, product features in the vicinity of the target, within the measurement spot, would interfere with the pupil image. Without an image, it is not possible to separate out the effect of the product features.

As already stated, a pupil image may be obtained from the plenoptic image. However, because the pupil image has been obtained from an array of real images (the plenoptic image), the plenoptic image can be inspected (e.g., using pattern recognition techniques) and the effect of the product structure can be filtered out. This can be done by identifying the sub-images which correspond to product structure and not using these when constructing the pupil image. In this way, a 2D angle resolved pupil image which is free of product structure can be obtained. This pupil image can be used in reconstruction.

In an alternative embodiment to that described, a simultaneous phase and amplitude angle-resolved scatterometer may comprise, as already described, a microlens array placed in the pupil plane with a sensor in its focal plane, thereby operating as a Shack-Hartmann type of wavefront sensor. Therefore, compared to a scatterometer of a type similar to the first measurement branch of FIG. 3(a), which only relays the pupil information towards a CCD camera, the pupil information may also be relayed (e.g., via a beam splitter) to the wavefront sensor. The wavefront sensor measures the local wave front gradient, which can be transformed into the wavefront by integration. In this type of scatterometer both the phase and the amplitude information, imprinted onto the illumination light by the target, can be measured simultaneously. Using more information for reconstruction purposes should make applications more robust to sensor imperfections and suboptimal measurement conditions, effectively increasing the application's "process window".

While the targets described above are metrology targets specifically designed and formed for the purposes of measurement, in other embodiments, properties may be measured on targets which are functional parts of devices formed on the substrate. Many devices have regular, grating-like structures. The terms 'target grating' and 'target' as used herein do not require that the structure has been provided specifically for the measurement being performed. Further, pitch P of the metrology targets is close to the resolution limit of the optical system of the scatterometer, but may be much larger than the dimension of typical product features made by lithographic process in the target portions C. In practice the lines and/or spaces of the overlay gratings within the targets may be made to include smaller structures similar in dimension to the product features.

In association with the physical grating structures of the targets as realized on substrates and patterning devices, an embodiment may include a computer program containing one or more sequences of machine-readable instructions describing methods of measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3, is already in production and/or in use, the invention can be implemented by the provision of updated computer program products for causing a processor to perform the modified step S6 and so calculate overlay error or other parameters with reduced sensitivity to structural asymmetry.

The program may optionally be arranged to control the optical system, substrate support and the like to perform the steps S2-S5 for measurement of asymmetry on a suitable plurality of targets.

While the embodiments disclosed above are described in terms of diffraction based overlay measurements (e.g., measurements made using the second measurement branch of the apparatus shown in FIG. 3(a)), in principle the same models can be used for pupil based overlay measurements (e.g., measurements made using the first measurement branch of the apparatus shown in FIG. 3(a)). Consequently, it should be appreciated that the concepts described herein are equally applicable to diffraction based overlay measurements and pupil based overlay measurements.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the present invention are presented in below numbered clause:

1. A metrology apparatus for measuring a parameter of a lithographic process, the metrology apparatus comprising:
   an optical system for measuring a target on a substrate by illuminating the target with measurement radiation and detecting the measurement radiation scattered by the target; and
   an array of lenses, each lens being operable to focus the scattered measurement radiation onto a sensor, said array of lenses thereby forming an image on the sensor such that said image comprises a plurality of sub-images, each sub-image being formed by a corresponding lens of said array of lenses.
2. A metrology apparatus according to clause 1 wherein said array of lenses comprises a plurality of similar lenses arranged in a regular 2D array.
3. A metrology apparatus according to clause 1 or 2 wherein said sensor is located at the image plane defined by said array of lenses.
4. A metrology apparatus according to clause 1, 2 or 3 wherein said array of lenses is located at a pupil plane of the optical system.
5. A metrology apparatus according to clause 1, 2 or 3 wherein said array of lenses is located between a pupil plane of the optical system and the image plane, and at a distance from the pupil plane equal to the focal length of each lens of said array of lenses.
6. A metrology apparatus according to clause 4 or 5 wherein said optical system comprises an output lens and an objective lens, said output lens being operable to form an image of a back focal plane of the objective lens at said pupil plane.
7. A metrology apparatus according to any preceding clause wherein said image is a plenoptic image.

8. A metrology apparatus according to any preceding clause wherein at least some of said sub-images are composed of higher orders of said scattered measurement radiation.
9. A metrology apparatus according to any preceding clause being operable to measure deviation of the positions of said sub-images relative to a regular 2D grid.
10. A metrology apparatus according to clause 9 wherein said metrology apparatus is operable to:

measure intensity asymmetry in corresponding higher orders of the scattered measurement radiation from said sub-images; and determine, from each of the measurements of intensity asymmetry, a local measurement of target asymmetry in a target being measured.

11. A metrology apparatus according to clause 10 being operable to combine said local measurements of target asymmetry in the target being measured, to obtain an overall measurement of target asymmetry.
12. A metrology apparatus according to clause 11 wherein said combining of said local measurements of target asymmetry includes weighting said local measurements of target asymmetry based on the deviation of the positions of the corresponding sub-images relative to a regular 2D grid.
13. A metrology apparatus according to clause 12 wherein said local measurements of target asymmetry are given greater weighting the closer the positions of its corresponding sub-image is to the regular 2D grid.
14. A metrology apparatus according to any of clauses 10 to 13 operable to:

obtain, in a single measurement step, a plurality of different values for intensity asymmetry from different corresponding pairs of sub-images of a target comprising a first grating and a second grating, wherein the target asymmetry of the first grating comprises a structural contribution due to structural asymmetry, a first imposed target asymmetry and an overlay error and the target asymmetry of the second grating comprises, the structural contribution due to structural asymmetry, a second imposed target asymmetry and the overlay error; and determine a value for the overlay error from said plurality of different values for intensity asymmetry.

15. A metrology apparatus according to clause 14 wherein said structural contribution due to structural asymmetry results in an offset in the relationship between target asymmetry and intensity asymmetry described by an offset term, and said determining a value for the overlay error comprises determining a value for said offset term.
16. A metrology apparatus according to 14 or 15 wherein said determining a value for the overlay error comprises plotting the intensity asymmetry measurements obtained from inspection of said first grating against asymmetry measurements obtained from inspection of said second grating.
17. A metrology apparatus according to any of clauses 9 to 16 being operable to determine whether said optical system is correctly focused based on said deviation of the positions of the sub-images relative to a regular 2D grid.
18. A metrology apparatus according to clause 17 being operable to:

obtain an image for each of a plurality of focus settings;
determine the relationship between focus and said deviation of the positions of the sub-images comprised with said images relative to a regular 2D grid; and
for subsequent images, determine focus from the deviation of the positions of the sub-images comprised within each subsequent image relative to a regular 2D grid and said determined relationship.

19. A metrology apparatus according to clause 18 being further operable to determine a static component in said deviation of the positions of the sub-images relative to a regular 2D grid and correcting for this static component.
20. A metrology apparatus according to any preceding clause operable to calculate a pupil image from intensities of the sub-images.
21. A metrology apparatus according to clause 20 being operable to:

determine a phase distribution from said pupil image; and
determine aberrations in the optical system from said phase distribution.

22. A metrology apparatus according to any preceding clause wherein said target is smaller than a measurement field of the metrology apparatus, such that a measurement of the target also comprises influence from structures adjacent the target; said metrology apparatus being operable to:

identify which of said sub-images result from measurement radiation scattered from said structures adjacent the target and which of said sub-images result from measurement radiation scattered from the target; and
reconstruct one or parameters of the target using only sub-images which result from measurement radiation scattered from the target.

23. A metrology apparatus according to any preceding clause wherein said target comprises two or more gratings having different pitches; said metrology apparatus being operable to identify which sub-image corresponds to which target by its location within the image.
24. A metrology apparatus according to clause 23 wherein said two or more gratings are composed of structures in different layer combinations, said metrology apparatus being operable to determine a value for target asymmetry for each of said layer combinations in a single measurement step.
25. A metrology apparatus according to clause 24 wherein the pitch of at least one of said gratings is such that sub-images of said grating are formed on the sensor from different magnitude higher orders; and said determination of a value for target asymmetry for each grating comprises using different sub-images with different weightings.

26. A lithographic system comprising:
a lithographic apparatus comprising:
an illumination optical system arranged to illuminate a pattern;
a projection optical system arranged to project an image of the pattern onto a substrate; and
a metrology apparatus according to any preceding clause, wherein the lithographic apparatus is arranged to use a determination of target asymmetry by the metrology apparatus in applying the pattern to further substrates.
27. A method of measuring a parameter of a lithographic process, comprising:

measuring a target on a substrate by illuminating the target with measurement radiation and detecting the measurement radiation scattered by the target;

forming an image of the target, said image comprising a plurality of sub-images, each sub-image being formed by a corresponding lens of an array of lenses; and
measuring said parameter of a lithographic process from said image.
28. A method according to clause 27 wherein said array of lenses comprises a plurality of similar lenses arranged in a regular 2D array.
29. A method according to clause 27 or 28 wherein said image is formed at the image plane defined by said array of lenses.
30. A method according to any of clauses 27 to 29 wherein the array of lenses is located at a pupil plane of an optical system used for performing the method.
31. A method according to any of clauses 27 to 29 wherein said array of lenses is located between a pupil plane of the optical system and the image plane, and at a distance from the pupil plane equal to the focal length of each lens of said array of lenses.
32. A method according to any of clauses 27 to 31 wherein said image is a plenoptic image.
33. A method according to any of clauses 27 to 32 wherein said sub-images are composed of higher orders of said scattered measurement radiation.
34. A method according to any of clauses 27 to 33 comprising measuring deviation of the positions of said sub-images relative to a regular 2D grid.
35. A method according to clause 34 comprising:
measuring intensity asymmetry in corresponding higher orders of the scattered measurement radiation from said sub-images; and
determining, from each of the measurements of intensity asymmetry, a local measurement of target asymmetry in a target being measured.
36. A method according to clause 35 comprising combining said local measurements of target asymmetry in the target being measured, to obtain an overall measurement of target asymmetry.
37. A method according to clause 36 wherein said combining of said local measurements of target asymmetry includes weighting said local measurements of target asymmetry based on the deviation of the positions of the corresponding sub-images relative to the regular 2D grid.
38. A method according to clause 37 wherein said local measurements of target asymmetry are given greater weighting the closer the positions of its corresponding sub-image is to the regular 2D grid.
39. A method according to any of clauses 35 to 38 comprising:
obtaining, in a single measurement step, a plurality of different values for intensity asymmetry from different corresponding pairs of sub-images of a target comprising a first grating and a second grating, wherein the target asymmetry of the first grating comprises a structural contribution due to structural asymmetry, a first imposed target asymmetry and an overlay error and the target asymmetry of the second grating comprises the structural contribution due to structural asymmetry, a second imposed target asymmetry and the overlay error; and
determining a value for the overlay error from said plurality of different values for intensity asymmetry.
40. A method according to clause 39 wherein said structural contribution due to structural asymmetry results in an offset in the relationship between target asymmetry and intensity asymmetry described by an offset term, and said determining a value for the overlay error comprises determining a value for said offset term.
41. A method according to 39 or 40 wherein said determining a value for the overlay error comprises plotting the intensity asymmetry measurements obtained from inspection of said first grating against asymmetry measurements obtained from inspection of said second grating.
42. A method according to any of clauses 34 to 41 comprising determining whether said optical system is correctly focused based on said deviation of the positions of the sub-images relative to a regular 2D grid.
43. A method according to clause 42 comprising:
obtaining an image for each of a plurality of focus settings;
determining the relationship between focus and said deviation of the positions of the sub-images comprised within said images relative to a regular 2D grid; and
for subsequent images, determining focus from the deviation of the positions of the sub-images relative to a regular 2D grid and said determined relationship.
44. A method according to clause 43 comprising determining a static component in said deviation of the positions of the sub-images relative to a regular 2D grid and correcting for this static component.
45. A method according to any of clauses 27 to 44 comprising calculating a pupil image from intensities of the sub-images.
46. A method according to clause 45 comprising:
determining a phase distribution from said pupil image; and
determining aberrations in the optical system from said phase distribution.
47. A method according to any of clauses 27 to 46 wherein said target is smaller than a measurement field of the metrology apparatus, such that a measurement of the target also comprises influence from structures adjacent the target; said metrology apparatus comprising:
identifying which of said sub-images result from measurement radiation scattered from said structures adjacent the target and which of said sub-images result from measurement radiation scattered from the target; and
reconstructing one or parameters of the target using only sub-images which result from measurement radiation scattered from the target.
48. A method according to any of clauses 27 to 47 wherein said target comprises two or more gratings having different pitches; said metrology apparatus comprising identifying which sub-image corresponds to which target by its location within the image.
49. A method according to clause 48 wherein said two or more gratings are composed of structures in different layer combinations, said metrology apparatus comprising determining a value for target asymmetry for each of said layer combinations in a single measurement step.
50. A method according to clause 49 wherein the pitch of at least one of said gratings is such that sub-images of said grating are formed on the sensor from different magnitude higher orders; and
said determining of a value for target asymmetry for each grating comprises using different sub-images with different weightings.
51. A computer program comprising processor readable instructions which, when run on suitable processor controlled apparatus, cause the processor controlled apparatus to perform the method of any one of clauses 27 to 50.

52. A computer program carrier comprising the computer program of clause 51.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A metrology apparatus comprising:
   an optical system comprising a sensor, the optical system configured to measure a target on a substrate by illuminating the target with radiation and, using the sensor, detecting the radiation scattered by the target; and
   an array of lenses configured to form an image on the sensor, the image comprising a plurality of sub-images, such that each of the sub-images is formed by a corresponding one of the lenses;
   wherein the optical system is further configured to:
      measure intensity asymmetries in respective higher orders of the sub-images; and
      determine, from the intensity asymmetries, a local target asymmetry, and
   wherein said sensor is located at the image plane defined by said array of lenses.

2. The metrology apparatus of claim 1, wherein said array of lenses is located at a pupil plane of the optical system.

3. The metrology apparatus of claim 1, wherein said array of lenses is located between a pupil plane of the optical system and the image plane, and at a distance from the pupil plane equal to the focal length of each lens of said array of lenses.

4. The metrology apparatus of claim 2, wherein said optical system comprises an output lens and an objective lens, said output lens being operable to form an image of a back focal plane of the objective lens at said pupil plane.

5. The metrology apparatus of claim 3, wherein said optical system comprises an output lens and an objective lens, said output lens being operable to form an image of a back focal plane of the objective lens at said pupil plane.

6. The metrology apparatus of claim 1, wherein said image is a plenoptic image.

7. The metrology apparatus of claim 1, wherein at least some of said sub-images are composed of higher orders of said scattered measurement radiation.

8. The metrology apparatus of claim 1 wherein said metrology apparatus is configured to:
   measure intensity asymmetry in corresponding higher orders of the scattered measurement radiation from said sub-images; and
   determine, from each of the measurements of intensity asymmetry, a local measurement of target asymmetry in a target being measured.

9. The metrology apparatus of claim 8, further configured to combine said local measurements of target asymmetry in the target being measured, to obtain an overall measurement of target asymmetry.

10. The metrology apparatus of claim 9, wherein said combining of said local measurements of target asymmetry includes weighting said local measurements of target asymmetry based on the deviation of the positions of the corresponding sub-images relative to a regular 2D grid.

11. The metrology apparatus of claim 10, wherein said local measurements of target asymmetry are given greater weighting the closer the positions of its corresponding sub-image is to the regular 2D grid.

12. The metrology apparatus of claim 8, further configured to:
   obtain, in a single measurement step, a plurality of different values for intensity asymmetry from different corresponding pairs of sub-images of a target comprising a first grating and a second grating, wherein the target asymmetry of the first grating comprises a structural contribution due to structural asymmetry, a first imposed target asymmetry and an overlay error and the target asymmetry of the second grating comprises, the structural contribution due to structural asymmetry, a second imposed target asymmetry and the overlay error; and
   determine a value for the overlay error from said plurality of different values for intensity asymmetry.

13. The metrology apparatus of claim 12, wherein said structural contribution due to structural asymmetry results in an offset in the relationship between target asymmetry and intensity asymmetry described by an offset term, and said determining a value for the overlay error comprises determining a value for said offset term.

14. The metrology apparatus of claim 12, wherein said determining a value for the overlay error comprises plotting the intensity asymmetry measurements obtained from inspection of said first grating against asymmetry measurements obtained from inspection of said second grating.

15. The metrology apparatus of claim 8, further configured to determine whether said optical system is correctly focused based on said deviation of the positions of the sub-images relative to a regular 2D grid.

16. The metrology apparatus of claim 1, further configured to:
   obtain an image for each of a plurality of focus settings;
   determine the relationship between focus and said deviation of the positions of the sub-images comprised with said images relative to a regular 2D grid; and
   for subsequent images, determine focus from the deviation of the positions of the sub-images comprised within each subsequent image relative to a regular 2D grid and said determined relationship.

17. The metrology apparatus of claim 16, further configured to determine a static component in said deviation of the positions of the sub-images relative to a regular 2D grid and correcting for this static component.

18. The metrology apparatus of claim 17, further configured to: calculate a pupil image from intensities of the sub-images;
　　determine a phase distribution from said pupil image; and
　　determine aberrations in the optical system from said phase distribution.

* * * * *

UNITED STATES PATENT AND TRADEMARK OFFICE
CERTIFICATE OF CORRECTION

| | | |
|---|---|---|
| PATENT NO. | : 10,423,077 B2 | Page 1 of 1 |
| APPLICATION NO. | : 16/223372 | |
| DATED | : September 24, 2019 | |
| INVENTOR(S) | : Pandey et al. | |

It is certified that error appears in the above-identified patent and that said Letters Patent is hereby corrected as shown below:

In the Claims

In Column 26, Claim 16, Lines 60-67, please delete:
"obtain an image for each of a plurality of focus settings; determine the relationship between focus and said deviation of the positions of the sub-images comprised with said images relative to a regular 2D grid; and for subsequent images, determine focus from the deviation of the positions of the sub-images comprised within each subsequent image relative to a regular 2D grid and said determined relationship."
And insert:
--calculate a pupil image from intensities of the sub-images; determine a phase distribution from said pupil image; and determine aberrations in the optical system from said phase distribution.--

In Column 27, Claim 18, Lines 6-10, please delete:
"calculate a pupil image from intensities of the sub-images; determine a phase distribution from said pupil image; and determine aberrations in the optical system from said phase distribution."
And insert:
--obtain an image for each of a plurality of focus settings;
determine the relationship between focus and said deviation of the positions of the sub-images comprised with said images relative to a regular 2D grid; and
for subsequent images, determine focus from the deviation of the positions of the sub-images comprised within each subsequent image relative to a regular 2D grid and said determined relationship.--

Signed and Sealed this
Eighth Day of December, 2020

Andrei Iancu
*Director of the United States Patent and Trademark Office*